United States Patent [19]

Cochran et al.

[11] Patent Number: 5,196,597
[45] Date of Patent: Mar. 23, 1993

[54] OXIDATION OF ISOBUTANE TO TERTIARY BUTYL HYDROPEROXIDE

[75] Inventors: Robert N. Cochran; Shaw-Chan Lin, both of West Chester, Pa.

[73] Assignee: Arco Chemical Technology, L.P., Wilmington, Del.

[21] Appl. No.: 872,794

[22] Filed: Apr. 22, 1992

[51] Int. Cl.$^5$ ............... C07C 179/02; C07C 27/12
[52] U.S. Cl. ............................ 568/571; 568/565; 568/569; 568/840; 568/910
[58] Field of Search ............ 568/571, 573, 840, 910, 568/569

[56] References Cited

U.S. PATENT DOCUMENTS

| | | | |
|---|---|---|---|
| 2,845,461 | 7/1958 | Winkler et al. | 568/910 |
| 3,351,635 | 11/1967 | Kollar | 549/523 |
| 3,478,108 | 11/1969 | Grane | 568/575 |
| 3,907,902 | 9/1975 | Grane | 568/571 |
| 4,404,406 | 9/1983 | Lutz et al. | 568/571 |
| 4,408,081 | 10/1983 | Foster | 568/571 |
| 4,408,082 | 10/1983 | Baumgarter | 568/571 |

*Primary Examiner*—Werren B. Lone
*Attorney, Agent, or Firm*—William C. Long

[57] ABSTRACT

The present invention relates to a process for the oxidation of isobutane in the liquid phase to produce TBA and TBHP wherein at least a portion of the oxidation product mixture is obtained from the condensate of vapors from the oxidation zone.

3 Claims, 1 Drawing Sheet

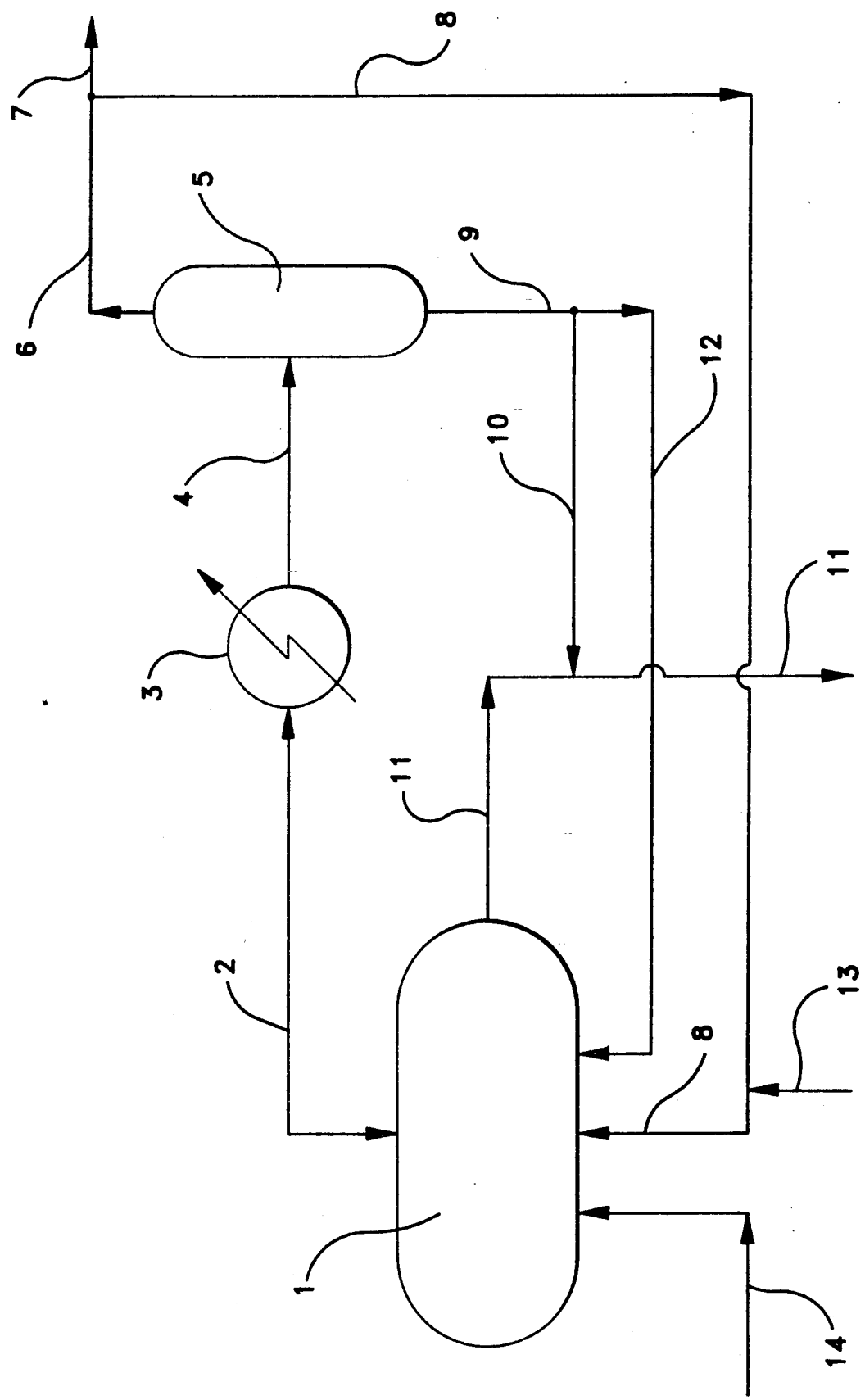

OXIDATION OF ISOBUTANE TO TERTIARY BUTYL HYDROPEROXIDE

BACKGROUND OF THE INVENTION

1. Field of the Invention

The present invention relates to the oxidation of isobutane to tertiary butyl hydroperoxide (TBHP) and to an improved method for carrying out the oxidation wherein at least a portion of the TBHP-containing liquid oxidation product is obtained from the condensate of vapors from the oxidation zone.

2. Description of the Prior Art

Methods are known for the production of TBHP by the molecular oxygen oxidation of isobutane at elevated temperature and pressure. In this regard, attention is drawn to U.S. Pat. No. 2,845,461 of Winkler, et al., to U.S. Pat. No. 3,478,108 of Grane and to U.S. Pat. No. 4,408,081 of Foster, et al. Frequently, the TBHP product from the oxidation is used to epoxidize olefins such as propylene by procedures such as those described in basic U.S. Pat. No. 3,351,635.

Problems associated with prior processes have been lower than desired reaction rates and greater than desired make of by-products. In addition, in some situations, due to fluctuation in market conditions, it is advantageous to produce more tertiary butyl alcohol (TBA) relative to the amount of epoxide which is formed by reaction of TBHP with olefin.

In accordance with the present invention, a straight-forward and simple method is provided for improving reaction rate, selectivity and product distribution which is readily applicable to existing commercial practice.

BRIEF DESCRIPTION OF THE INVENTION

In practice of the present invention, isobutane is oxidized in the liquid phase with molecular oxygen to form tertiary butyl hydroperoxide (TBHP) as well as tertiary butyl alcohol (TBA) in accordance with known and conventional procedures. During the process, a vapor mixture comprised of unreacted oxygen, inerts, isobutane, TBHP and TBA is removed from the oxidation reaction zone and cooled to condense the readily condensible components, TBHP and TBA, from non-condensibles such as oxygen and inert gases including carbon oxides, nitrogen and the like. As an essential feature of the invention, at least a portion of the TBA- and TBHP-containing condensate is separated as an oxidation product stream rather than being recycled to the oxidation zone as has been the prior practice.

DESCRIPTION OF THE DRAWING

The accompanying drawing illustrates in schematic form practice of the invention.

DETAILED DESCRIPTION

The invention can best be described with reference to the accompanying drawing. Referring to the drawing, isobutane is reacted with oxygen in reactor 1 to produce TBHP along with TBA. The isobutane oxidation reaction conditions in oxidation reactor 1 are those which are normally used for this reaction as described, for example, in Winkler, et al. U.S. Pat. No. 2,845,461. Generally, reaction temperatures in the range of 100° C. to 200° C., preferably 120° C. to 150° C. are employed. Pressures in the range of 200 to 500 psig, preferably 300 to 450 psig are employed. Residence times in the oxidation zone of 3 to 15 hours, preferably 5 to 10 hours are suitable. It is preferred to use oxygen as the oxidant, although the use of oxygen in admixture with minor amounts of an inert gas such as nitrogen can be used.

As a result of the isobutane oxidation in reaction zone 1, both TBHP and TBA are produced. Generally, the weight ratio of TBA to TBHP produced in reaction zone 1 is less than 0.8. In order to remove the exothermic heat of reaction, conditions of the reaction in zone 1 are regulated such that the reaction mixture is constantly boiling with vapors being removed from zone 1 by means of line 2. Vaporization results in the removal of the exothermic heat of reaction.

The weight ratio of TBA to TBHP in the vapors which are removed from zone 1 is generally above about 1.0 due to the relative boiling points of these materials. Also contained in the vapor stream from zone 1 is unreacted isobutane, unreacted molecular oxygen and inert materials.

In accordance with the invention, the vapors from zone 1 pass via line 2 to condenser 3 wherein the vapors are cooled in order to condense the readily condensible materials, specifically isobutane, TBA and TBHP. From cooler 3 the cooled materials pass via line 4 to decanter or knock out drum 5 wherein the vapors and liquid condensate are separated. The uncondensed materials pass from zone 5 via line 6 with a portion purged via line 7 and the remainder recycled via line 8 to oxidation zone 1.

As an essential feature of the present invention and presenting a distinct departure from prior practices, the liquid condensate comprised of isobutane, TBA and TBHP passes from zone 5 via line 9, and at least a portion of this liquid condensate is recovered by means of lines 10 and 11 as a product of the isobutane oxidation.

The advantage of this mode of operation is that the liquid stream from knock-out drum 5, which is relatively concentrated in TBA, is recovered as a product of the oxidation rather than being recycled back to the oxidation 20 zone 1. In prior practices, liquid condensate from the knock out drum was recycled in its entirety to the oxidation zone. This procedure resulted in relatively high concentrations of TBA in the oxidation zone which in turn caused both inhibition of the isobutane oxidation and loss of selectivity to undesirable by-products such as acetone.

Depending on the particular economics of a practice of the invention, from about at least 5% to as high as 95% of the liquid condensate from knock out pot 5 can be recovered as product by means of line 10 and 11. Where economic circumstances dictate, up to 95% of this condensate can be recycled to zone 1 by means of line 12.

Molecular oxygen is introduced into oxidation zone 1 by means of lines 13 and 8 and fresh and recycled isobutane is fed to zone 1 via line 14.

Liquid oxidation product from zone 1 can be recovered by means of line 11, and when combined with the liquid condensate product from zone 5, comprises the overall liquid product of the oxidation taking place in zone 1.

As pointed out above, practice of the present invention has some important advantages when contrasted with the procedures of the prior art. The rate of oxidation and the selectivity of the oxidation to the desired TBA product is significantly improved as a result of the recovery of at least a portion of the liquid condensate as product from knock out drum 5. In addition, practice of the present invention provides added flexibility in the determination of the relative amounts of TBA and TBHP which are produced by the oxidation. This latter feature is of special significance since the TBHP normally is employed in the production of an epoxide such as propylene oxide. The added flexibility achieved by this process enables the overall process to be practiced more economically depending on the economic requirements at any particular time.

To further illustrate the invention, the following example is presented based on the process described in the attached drawing.

Isobutane in the amount of 89,340 lbs./hr. representing both net fresh isobutane as well as recycle isobutane is introduced into reaction zone 1 by means of line 14. Molecular oxygen in amount of 16,400 lbs./hr. is introduced into zone 1 by means of line 13, the molecular oxygen representing >99% of this stream, the remainder being inerts which are primarily nitrogen. Recycle vapors having the composition 72.3 wt.% isobutane, 13.7 wt.% TBA, 8.2 wt.% TBHP and other minor components in amount of 376,430 lbs./hr. passes via line 8 to oxidation zone 1.

The oxidation conditions maintained in zone 1 are a temperature of 137° C. and a pressure of 341 psig. Continuously removed from zone 1 via line 2 is a vapor mixture comprised of 61.3 wt.% isobutane, 18.2 wt.% TBA, 15.5 wt.% TBHP and 0.8 wt.% molecular oxygen. This stream is removed at the rate of 742,920 lbs./hr. and passes to cooler 3 wherein it is cooled by indirect heat exchange to a temperature of 124° C. The cooled mixture passes via line 4 to knock out drum 5 wherein the liquid condensate and uncondensed vapors are separated. Uncondensed vapors having a composition by weight of 72.3% isobutane, 1.5% molecular oxygen, 8.2% TBHP and 13.7% TBA are separated at the rate of 380,160 lbs./hr. via line 6. A portion of this stream in amount of 3,730 lbs./hr. is separated via line 7 as purge with the remainder being recycled via line 8 to oxidation zone 1.

Liquid condensate is removed from knock out drum 5 by means of line 9. The composition by weight of this stream is 49.8% isobutane, 22.9% TBA and 23.0% TBHP. About 87,600 lbs./hr. of this condensate stream is separated via line 10 and represents a product of the isobutane oxidation. About 275,160 lbs./hr. of this stream passes via line 12 back to oxidation zone 1.

A liquid oxidation reaction mixture stream having the composition by weight 24.1% TBA, 32.0% TBHP and 38.2% isobutane is removed from zone 1 via line 11 and also represents a product of the oxidation process.

From the above it can be seen that the TBA to TBHP weight ratio in the product stream from the knock-out drum is significantly higher than that of the liquid stream from reactor 1. In addition, the reaction rate is substantially improved and the make of undesirable by-products is substantially less as contrasted with conventional procedures.

We claim:

1. The process for the oxidation of isobutane to produce tertiary butyl alcohol and tertiary butyl hydroperoxide wherein isobutane is reacted with molecular oxygen in the liquid phase at 100°–200° C., a vapor stream comprised of tertiary butyl alcohol and tertiary butyl hydroperoxide is continuously removed during the oxidation from the oxidation zone and condensed, and 5 to 95% of the liquid condensate comprised of tertiary butyl alcohol and tertiary butyl hydroperoxide is recovered as a product of the oxidation.

2. The method claim 1 wherein 5 to 95% of the said condensate is recovered as product with the remaining 5 to 95% being recycled to the oxidation.

3. The method of claim 1 wherein the weight ratio of tertiary butyl alcohol to tertiary butyl hydroperoxide is said condensate is above about 0.8.

* * * * *